United States Patent [19]

Homcy et al.

[11] 4,332,787
[45] Jun. 1, 1982

[54] ASSAY FOR BETA-ADRENERGIC ANTAGONISTS AND ANTIBODY THEREFOR

[75] Inventors: Charles J. Homcy; Edgar Haber, both of Weston, Mass.

[73] Assignee: The Massachusetts General Hospital, Boston, Mass.

[21] Appl. No.: 162,081

[22] Filed: Jun. 23, 1980

[51] Int. Cl.³ .................... G01N 33/56; G01N 33/58; C07G 7/00
[52] U.S. Cl. ..................................... 424/1; 23/230 B; 260/112 B; 424/12; 424/85
[58] Field of Search .............................. 424/1, 12, 85; 23/230 B; 260/112 B

[56] References Cited

U.S. PATENT DOCUMENTS 4,026,879 5/1977 Spector .......................... 260/112 B
4,070,492 1/1978 Spector ................................. 424/1

OTHER PUBLICATIONS

Mueller et al., From Radio Immunoassay of Drugs and Hormones in Cardiovascular Medicine, Ed. Albertine et al., Elsevier/North-Holland, The Netherlands, 1979, pp. 93-106.

Primary Examiner—Christine M. Nucker
Attorney, Agent, or Firm—Paul J. Cook; Marvin C. Guthrie

[57] ABSTRACT

Body fluids are assayed for aryloxypropylamine beta-adrenergic antagonists and/or their active metabolites by agglutination reaction with antibody for the antagonist and/or active metabolite. The antibody is produced from an antigen comprising a conjugate of an immunogenic protein linked by a diazo moiety to an aryloxypropylamine beta-adrenergic antagonist.

14 Claims, 3 Drawing Figures

ASSAY FOR BETA-ADRENERGIC ANTAGONISTS AND ANTIBODY THEREFOR

The Government has rights in this invention under Grant No. 1-T32-HL07416 from the National Institute of Health.

BACKGROUND OF THE INVENTION

This invention relates to a process for determining the concentration of beta-adrenergic antagonists and their active metabolites in body fluids, antibodies useful in the assay and the method for obtaining the antibodies.

Presently, beta-adrenergic antagonists comprising the aryloxypropylamine series are widely used in the treatment of various cardiovascular diseases including angina pectoris, unstable angina, ventricular arrhythmia as well as primary and secondary forms of hypertension, thyrotoxicosis and migraine headaches. Examples of these drugs include propranolol, alprenolol hydrochloride, pindolol, tazolol, butoxamine hydrochloride and the like. Despite the widespread utility of these drugs, the maximal application in these clinical situations has been hampered by a relative inability to ascertain the end point of therapy. Propanolol, for example, is a drug with markedly variable bio-availibility and the desired therapeutic response bears little relationship to the dose administered. Furthermore, the drug has very few side effects, but its undesired side effects represent, in large part, an excess of the desired pharmacological response. To varying degrees, the same problem exists with the other forms of the aryloxypropylamine beta-adrenergic antagonists.

Physicians rely heavily upon documentation of a basal sinus bradycardia as a reflection of an adequate drug dose. However, this single clinical parameter dos not necessarily bear a predictable relationship to the adequate suppression of catecholamine effects with maximal exercise which is a better measure of sufficient beta-adrenergic blockade. This approach is more reliable and can be carried out in an exercise laboratory, but it is clearly an expensive, time-consuming approach which is not applicable to this serial evaluation of chronically ill patients.

Many prior attempts have been made to employ laboratory methods for the detection of propranolol in body fluids. These methods, which include fluorometric assay, radioreceptor assay and organic extraction with gas chromatography, share the features of relative insensitivity, excessive cost, or excessive time required for the processing of a single sample, making the approach unwieldy for large numbers of determinations or repeated determinations in a single patient. Furthermore, it has been documented that when the drug is orally administered, a significant fraction of the administered dose is converted by the liver to 4 OH-propranolol, a metabolite which retains full biological activity in its ability to bind to the beta-adrenergic receptor. High performance liquid chromatography, unlike many other methods, has been demonstrated to reliably measure this active metabolite. Nevertheless, high performance liquid chromatography is undesirable due to its excessive cost and time for the manipulation of blood samples. Naphthoxylactic acid is a second major metabolite of propranolol which, unlike 4 OH-propranolol, bears no biological activity. An additional drawback of several of the methods proposed for the measurement of propranolol in serum is the inability to distinguish this inactive metabolite from the native drug and the other active metabolites.

It has been proposed by Hoebeke et al, Biochemical Pharmacology, Vol. 27, pp. 1527–1532, (1978) to utilize a sensitive radioimmunoassay approach for propranolol and other beta-adrenergic blocking drugs. In this procedure, a specific antibody is raised in rabbits immunized with alprenolol hydrochloride (a cogenor of propanolol)covalently linked to bovine serum albumin. The covalent linkage is accomplished by reacting the olefin moiety of the alprenolol with N-bromosuccinimide to yield the corresponding bromohydrin. This bromohydrin then is reacted with blood serum albumin which has been reduced with dithiothreitol, to form the reactive sulfhydryl group. The covalent linkage is accomplished in an inert atmosphere in the dark by mixing the two reactants in solution at about 4° C. for about 48 hours. The product then is purified such as by dialysis against deionized water. This conjugate in a phosphate buffered saline is administered intravenously to rabbits to raise the antibody which is recovered from the animals. The procedure is undesirable since the process of forming the bromide derivative is not high-yield. The process is also complicated by the fact that SH-groups must be substituted onto the protein carrier. Furthermore, the procedure is undesirable since the quantity of the antibody obtained from an animal is low so that the cost of immunization and subsequent recovery of antibody is undesirably expensive. These drawbacks outweigh the prime advantage of the Hoebeke et al process; namely, the antibody obtained is capable of determining the presence of other beta-adrenergic blocking drugs such as acebutolol, alprenolol, propranolol or other drugs which have the active propranolamine or ethanolamine side chain as well as active metabolites, but not the inactive metabolites.

It would be highly desirable to provide a means for assaying the concentration of beta-adrenergic antagonists as well as their active metabolites while avoiding the detection of inactive metabolites. Furthermore, it would be desirable to provide such an assay which utilizes an antibody that can be obtained from a given animal in much larger amounts than presently available antibodies. In addition, it would be desirable to provide a simplified procedure for raising such an antibody.

SUMMARY OF THE INVENTION

This invention provides a class of antibodies any one of which is useful for assaying for beta-adrenergic antagonists of the class which includes a side-chain having an ethanolamine group. The antibodies are obtained by administering to an animal an antigen comprising a conjugate of an immunogenic protein coupled, by means of a diazo linkage, to a beta-adrenergic antagonist or a derivative thereof which has a side-chain including an ethanolamine group. The antibody is harvested from the animal's blood serum, purified and radiolabeled so that it can be utilized to assay the plasma or blood serum of a patient for the beta-adrenergic antagonist and/or their active metabolites. Alternatively, the assay can be conducted by inhibition agglutination wherein a known sample of beta-adrenergic antagonist antigen is radiolabeled.

DESCRIPTION OF SPECIFIC EMBODIMENTS

Figure 1:
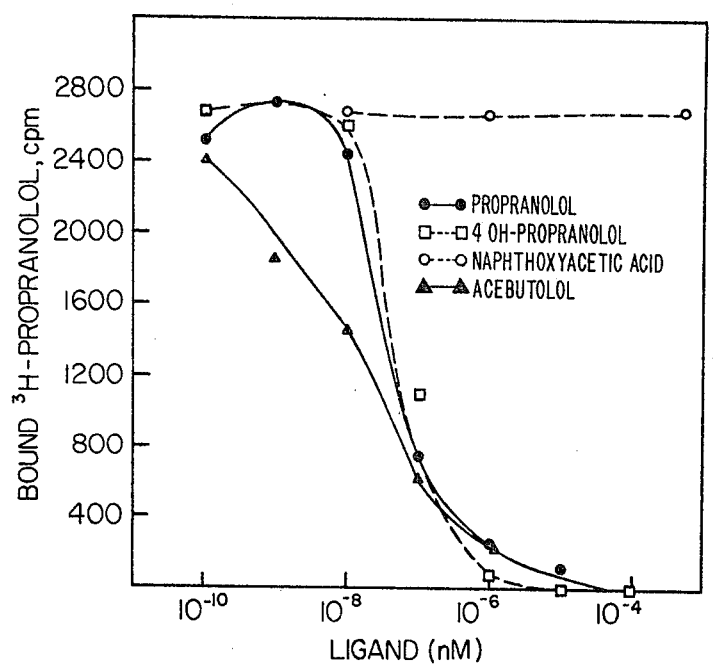
FIG. 1 is a binding inhibition curve.

The beta-adrenergic drugs or derivatives thereof which are coupled with an immunogenic protein through a diazo linkage are represented by the formula:

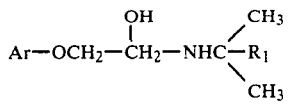

wherein Ar is a substituted or unsubstituted aryl group including phenyl, biphenyl or indolyl and $R_1$ is hydrogen, benzyl or p-hydroxy benzyl. Examples of suitable beta-adrenergic drugs and/or their derivatives are as follows:

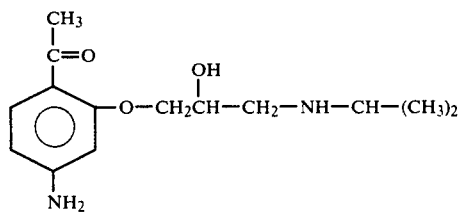

Acebutolol Amine

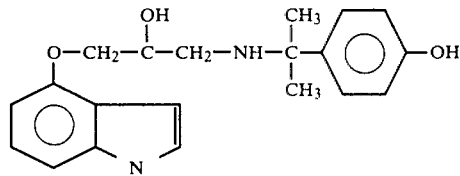

Hydroxybenzyl Pindolol

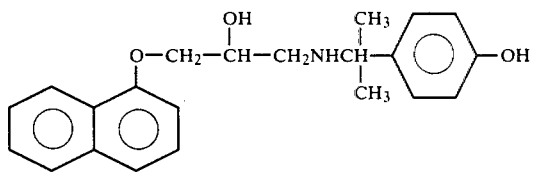

Hydroxybenzyl Propranolol

The compound acebutolol amine is available from May and Baker Corporation as compound M & B 17 127. Hydroxybenzyl pindolol is obtained from Sandoz, Switzerland.

The method of diazotization depends upon the beta-adrenergic drug or derivative thereof being converted. In the case of a compound having an amine substitution on the aryl group, diazotization is accomplished by reacting the compound with an alkali metal nitrite in the presence of a molar excess of acid. Typically, reaction is effected in an aqueous solvent such as 0.5 N HCl at a temperature of 0° C. for a period of time of between about 5 and about 15 min. After this initial reaction step, an immunogenic protein such as bovine serum albumin is added to the reaction mixture in the presence of sodium carbonate, 10% until a noticeable and permanent color change of the reaction medium is effected. Generally, this occurs in minutes. The reaction is allowed to proceed for about 1 hour between about 0° C. and about 4° C. The diazotized conjugate then is purified such as by dialysis against phosphate buffered saline or by gel filtration. The purified, diazotized conjugate then is further concentrated by lyophilization and then stored in an inert solvent at a temperature below about $-20°$ C. until it is to be administered to an animal in order to produce the desired antibody.

Coupling of a beta-adrenergic drug or derivative thereof having an hydroxyphenyl substitutent at the ethanolamine side-chain to an immunogenic protein is effected in two steps. In the first step, the drug is reacted with the diazonium salt of p-aminobenzoic acid. The reaction changes to a dark red and the reaction is allowed to proceed from about 1 hour. This complex is then reacted with an immunogenic protein in the presence of a 20-fold molar excess of water-soluble carbodiimide to form the ligand-protein conjugate. The resultant conjugate then is purified in a conventional manner such as by the procedure set forth above.

Representative suitable immunogenic proteins include bovine serum albumin, hemocyanin, thyrogobulin or the like.

Animals such as rabbit, goat, mouse or guinea pig then are immunized by injecting the conjugate suspended in a physiologically acceptable carrier such as Freund's adjuvant over a period of about 3 months during which time, injections are repeated periodically such as one a month. In order to recover the antibody, the animal is bled and the serum assayed at 1:10 dilutions for antibody activity.

The antibodies prepared in accordance with this invention are recovered in amounts at least in order of magnitude greater than those obtained by binding to immunogenic proteins utilizing a process involving reaction of bromohydrin. This is thought to result from the fact that the acebutolol derivatized protein is probably 10-fold more highly substituted than can be achieved with the alprenolol bromohydrin method of Hoebeke.

The following example illustrates the present invention and is not intended to limit the same.

EXAMPLE I

Preparation of the Immunogen

Acebutolol amine having the formula:

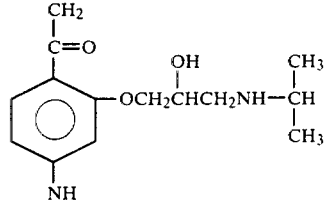

was covalently linked to lysozyme. 150 mg of acebutolol amine was dissolved in 1.0 N HCl and was cooled to 0° C. in a salt ice bath. To this solution was added 1 cc of 0.5 M $NaNO_2$ also at 0° C. and the resultant mixture was allowed to stand at 0° C. for 10 min. A mixture of 200 mg crystalline lysozyme in 15% aqueous sodium carbonate at 0° C. was added to 2.0 cc of the above mixture. A dark red color change was noted and reaction was continued at 0° C. for 1.5 hours. The resultant product was dialyzed against phosphate buffered saline and the purified conjugate was frozen in dry ice-acetone and stored at −20° C. The product then was thawed and centrifuged for 10 min at 3000 rpm. The supernatant was recovered and mixed with Tris buffer, pH 7 at a concentration of 30 mg/ml. Substitution of at least 5 mol acebutolol amine per mol protein was accomplished.

Albino rabbits were immunized with this conjugate at monthly intervals for four months. Each rabbit received intracutaneous toepad injections of 0.5 mg of protein emulsified in complete Freund's adjuvant.

Propranolol Radioimmunoassay

The assays were performed in triplicate. To each tube was added: 50 μl of immune serum, diluted 1:10 in phosphate buffered saline; 25 μl of a 4 nM solution of $^3$H-(−)-propranolol, specific activity 74 mCi/mg (Amersham); and 25 μl of the serum sample for propranolol quantitation. The $^3$H-(−)-propranolol was obtained from New England Nuclear Corporation. Serum samples with high propranolol levels were diluted with pooled human serum in order to bring drug concentration into range. The standard curve for the radioimmunoassay was derived from triplicate assay of pooled human serum containing varying amounts of added (±) propranolol HCl. For each determination, an identical volume of preimmune serum was assayed as a control for antibody binding. Total binding of $^3$H-(−)-propranolol to the antibody was determined in the presence of pooled human serum without added, unlabeled (±) propranolol. After an incubation period of 1 hr at 25° C., 100 μl of goat-antirabbit 1 gG antiserum was added to each tube with 50 μl of normal rabbit 1 gG as a carrier for the precipitation. The tubes were again incubated at 25° C. for 30 min. The precipitates were washed twice in Tris buffer and spun in a Sorvall tabletop centrifuge at 2,000 rpm × 10 min. After the supernatant was decanted, the precipitates were dissolved in 1 ml of 1% sodium dodecyl sulfate. Bound radioactivity was counted in the presence of 10 ml of Aquasol-2 (New England Nuclear) in a Packard Tricarb liquid scintillation counter with a counting efficiency of 40%. To determine the antibody binding characteristics, $^3$H-(−)-alprenolol, 58 Ci/mM (New England Nuclear), unlabeled (−)propranolol (Ayerst), unlabeled 4-OH-propranolol (Ayerst), unlabeled naphthoxyacetic acid (Sigma) and unlabeled acebutolol amine acid were individually examined.

Samples for the quantitation of propranolol disappearance rates from serum were obtained at standard time intervals following the intravenous administration of 10 mg of propranolol to healthy adult male volunteers. The assays to determine the competitive binding of potentially cross-reactive drugs were performed on sera obtained from patients on long-term maintenance with single drugs; digoxin, imipramine and alphamethyldopa, respectively.

Immunization of rabbits with the acebutolol-albumin conjugate elicited the production of an antibody which avidly binds beta adrenergic blocking agents. Competitive binding inhibition with (±) propranolol displayed an apparent $K_D$ of $10^{-8}$ M, indicating a high affinity of the binding site for this ligand.

Utilizing antiacebutolol amine immune serum, a radioimmunoassay for propranolol was devised. The standard radioimmunoassay curve indicates the quantitative displacement of antibody-bound $^3$H-propranolol by the added unlabeled (±)-propranolol. In the figures, each ordinate value represents the mean of triplicate determinations of antibody-bound $^3$H-propranolol. The radioactivity retained by the precipitates of preimmune serum comprised less than 10% of the total propranolol binding capacity and was subtracted from all values. At each concentration of unlabeled propranolol, antibody binding is expressed on the ordinate as a ratio. The assay was sensitive to less than 3 ng/ml of (±) propranolol. Standard deviation of the replicate data points was less than 5% of the total specific binding. The coefficient of variation for the assay was 0.05. Thus, the assay has the requisite reproducibility and sensitivity for clinical and experimental application.

Figure 2:
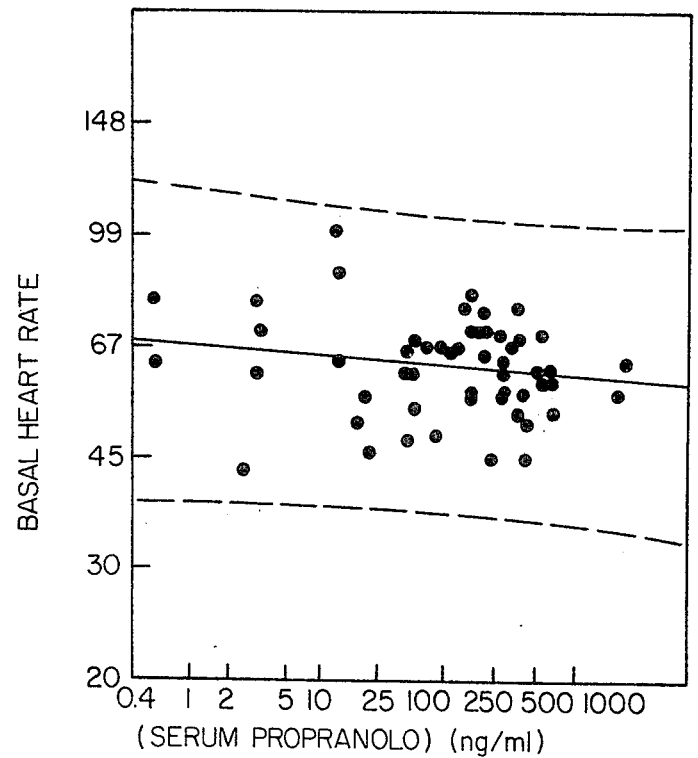
FIG. 2 is a serum propanolol disappearance curve.

The application of this radioimmunoassay to the measurement of propranolol levels in normal subjects also was investigated. Following the intravenous administration of a single 10 mg dose of propranolol to 3 adult volunteers, serial serum drug concentration were determined by radioimmunoassay by the aforementioned procedure. A representative serum propranolol disappearance curve is illustrated in FIG. 2, indicating a half-life for the drug of approximately 7.5 hours. The range of serum half-life observed in these subjects (5–7.5 hrs) demonstrated reasonable agreement with early pharmacodynamic estimations. As previously observed, the drug remains detectable in serum for six to twelve hrs following a single intravenous administration. To further document the reproducibility of the assay, each serum sample from a single subject was assayed in replicate fashion at dilutions of 1:2, 1:3 and 1:4 in pooled human serum. When corrected for dilution, close agreement was observed.

The metabolic fate of propranolol has been well documented, both in humans and in animal species. Besides its degradation to naphthoxylactic acid, a pharmacologically inactive major urinary metabolite, it has been demonstrated that extensive 4-hydroxylation of native propranolol occurs in all animal species. This metabolite, which is an equipotent beta adrenergic receptor antagonist, is detectable in serum only after the oral route of drug administration. In order to establish the requisite capacity of this assay to detect active metabolites, the binding capacity of the antibody for 4-hydroxypropranolol was investigated in pooled human sera to which known concentrations of the metabolite had been added (FIG. 1). The resultant competitive displacement curve demonstrates an apparent $K_D$ of $10^{-8}$ M, identical to the antibody binding affinite for native drug. In addition, when standard dilutions of 4-hydroxypropranolol were quantitated against the (±) propranolol standard radioimmunoassay curve, accurate detection of the added metabolite was demonstrable. In contrast, an inactive metabolite, which lacks the ability to bind to the beta adrenergic receptor, fails to compete for the antibody binding sites. Thus, naphthoxyacetic acid, a congener of the inactive propranolol metabolite, does not measurably inhibit binding of $^3$H-propranolol (FIG. 1).

Sera containing dogoxin, imipramine, (−)-norepinephrine, alpha methyldopa and dopamine all failed to produce significant competitive inhibition of $^3$H-propranolol binding to the antibody. However, assay of these same sera after the addition of 240 ng/ml of unlabeled propranolol resulted in the accurate measurement of the added drug. This antibody, raised against lysozyme conjugated acebutolol amine also displays specificity and high affinity for the propranolamine moiety in other beta adrenergic antagonists. For example, competitive binding inhibition with acebutolol amine (FIG. 1) yields a curve analogous to the displacement binding observed with propranolol.

To investigate the clinical utility of this radioimmunoassay for propranolol, prospective analysis of drug levels was undertaken in 54 patients who underwent cardiovascular stress testing in the exercise laboratory. All patients presented for exercise testing had a history of longterm, oral beta adrenergic blockade with propranolol and were consecutively selected for the determination of serum propranolol concentrations. The patients ranged in age from 32 to 77 years (mean age 55 years) and received between 0.2 and 11.5 mg/kg/day of propranolol (mean 1.9 mg/kg/day). All subjects were submitted to standard, graded exercise according to the Bruce protocol, and 36 of 54 patients attained at least Stage II of exertion (greater than 6 min of sustained exertion).

Figure 3:
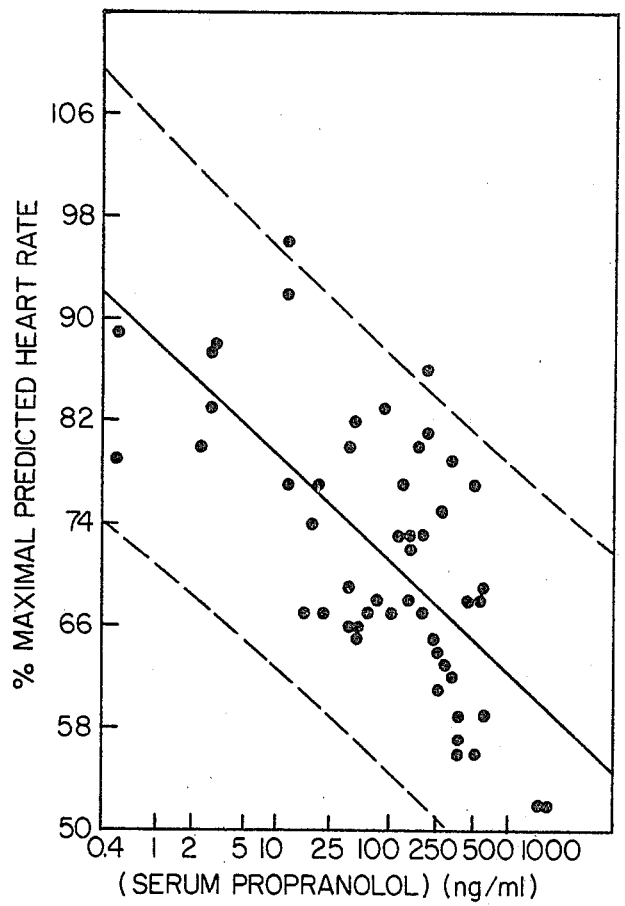
FIG. 3 shows heart rate vs. serum propanolol concentration.

An attempt was made to correlate plasma propranolol concentration with basal heart rate, exercise-induced change in blood pressure and heart rate, and the maximal attained heart rate, expressed as a percentage of the maximal response predicted for age (24). Basal heart rate, commonly used for the clinical assessment of beta blockade, failed to show any significant relationship either to plasma concentration (FIG. 2), response to exercise, or administered dose of propranolol. There was a similar lack of correlation between increases in blood pressure or heart rate and serum concentration of propranolol. However, when the percent of maximal predicted heart rate for age was plotted against the serum propranolol concentration, a correlation was observed (FIG. 3). A highly significant linear relationship ($p<0.0005$) between exercise response and serum propranolol concentrations was described by the linear regression analysis.

Utilizing this relationship, indicated in FIG. 3, the theoretical predictions were investigated for the serum propranolol concentration which should produce a desired extent of beta-adrenergic blockade. A serum propranolol concentration of 250 ng/ml ($\sim 1$ $\mu$mol/L) can be expected to inhibit fully the in vivo binding of catecholamines to tissue receptors, even with endogenous catecholamine concentrations which are known to occur in states of maximal stress; a serum propranolol concentration of 250 ng/ml will completely block the agonistic effects of even 10 nM norepinephrine, a catecholamine level commonly observed at the peak of strenuous exertion. Assuming an ideal concentration of 250 ng/ml, the derived relationship between serum propranolol and exercise heart rate predicts an exercise response of 67% of the maximal response expected for age. For most of the patients in this study, this was equivalent to a heart rate of $\leq 120$/min, a doubling of the conventionally accepted basal heart rate with adequate beta-blockade. In this study, only 3/33 of those patients with a serum level $<250$ ng/ml achieved an exercise response of $<67\%$ of predicted, whereas 10/16 patients with levels of $>250$ ng/ml exhibited an exercise response consistent with adequate beta-adrenergic blockade. Furthermore, when the average daily dose of propranolol in the adequately blocked patients ($2.45\pm2.89$ mg/kg/day) was compared to that of the inadequately blocked patients ($1.14\pm0.62$), the difference was also highly significant ($p<0.001$).

Thus, in this study of 56 patients, the correlation of serum propranolol and the heart rate response to maximal exercise was highly significant and predicted a linear relationship between these two variables. Thus, the adequacy of beta-adrenergic blockade can be accurately assessed by the radioimmunoassay of propranolol in serum, and that most patients with serum levels $\geq 250$ ng/ml can be assumed to have achieved therapeutic advantage from the drug.

We claim:
1. The process for determining the concentration of a material selected from the group consisting of an aryloxypropylamine beta-adrenergic antagonist or an active metabolite of said antagonist and mixtures thereof in a sample which comprises:
   a. mixing the sample with an antibody for said material, said antibody being formed from an antigen comprising a conjugate of an immunogenic protein linked by a diazo moiety to (a) an aryloxypropylamine beta-adrenergic antagonist or (b) a derivative of said antagonist having beta-adrenergic activity which derivative includes an aryloxypropylamine moiety,
   b. determining the extent of the binding reaction between said antibody and said material, and,
   c. comparing the measured extent of binding of an unknown with a known quantitative relationship between extent of binding and concentration of said material.
2. The process of claim 1 wherein said binding reaction is effected by mixing a sample of said material labeled with a radioactive isotope with said antibody to effect binding of said material with said antibody and separating said material bound to said antibody.
3. The process of claim 1 wherein said agglutination reaction is effected by mixing a sample of said material with a known concentration of said antibody, said concentration being in excess of that required for complete reaction of said material thereby to form a composition containing unreacted antibody, reacting said composition with said material labeled with a radioactive isotope and determining the extent of agglutination between said composition and said labeled material.
4. The process of claim 2 wherein said radioactive isotope is selected from the group consisting of tritium and iodine.
5. The process of claim 3 wherein said radioactive isotope is selected from the group consisting of tritium and iodine.
6. The process of any one of claims 1, 2, 3, 4 or 5 wherein said antigen is acebutolol amine linked to an immunogenic protein through a diazo moiety.
7. The process of any one of claims 1, 2, 3, 4 or 5 wherein said antigen is hydroxybenzyl propranolol linked to an immunogenic protein through a diazo moiety.
8. The process of any one of claims 1, 2, 3, 4 or 5 wherein said antigen is hydroxybenzyl pindolol linked to an immunogenic protein through a diazo moiety.
9. An antibody produced by incubating in the serum of an animal an antigen comprising a conjugate of an immunogenic protein linked by a diazo moiety to (a) an aryloxypropylamine beta-antagonist or (b) a derivative of said antagonist having beta-adrenergic activity which derivative includes an aryloxypropylamine moiety and recovering said antibody from said serum, said antibody being reactive with an aryloxypropylamine beta-adrenergic antagonist or a metabolite of said antagonist having beta-adrenergic antagonist activity.
10. The antibody of claim 9 wherein said immunogenic protein is linked to acebutolol amine.

11. The antibody of claim 9 wherein said immunogenic protein is linked to hydroxybenzyl pindolol.

12. The antibody of claim 9 wherein said immunogenic protein is linked to hydroxybenzyl propranolol.

13. The antibody of any one of claims 9, 10, 11 or 12 wherein said immunogenic protein is blood serum albumin.

14. The antibody of any one of claims 9, 10, 11 or 12 wherein said immunogenic protein is hemocyanin.

* * * * *